(12) United States Patent
Giovagnoli et al.

(10) Patent No.: US 9,359,629 B2
(45) Date of Patent: Jun. 7, 2016

(54) CELL CULTURE PROCESSES

(75) Inventors: Andre Giovagnoli, Viller-le-Lac (FR); Sylvain Roy, Savagnier (CH); Veronique Ducros, Champange (CH); Virginie Charlot, La Chaux-de-Fonds (CH); Yves-Olivier Stauffer, Epalinges (CH)

(73) Assignees: Baxalta Incorporated, Bannockburn, IL (US); Baxalta GmbH, Glattpark (Opfikon) (CH)

(*) Notice: Subject to any disclaimer, the term of this patent is extended or adjusted under 35 U.S.C. 154(b) by 853 days.

(21) Appl. No.: 12/341,807

(22) Filed: Dec. 22, 2008

(65) Prior Publication Data

US 2009/0176269 A1    Jul. 9, 2009

Related U.S. Application Data

(60) Provisional application No. 61/009,328, filed on Dec. 27, 2007.

(51) Int. Cl.
    *C12P 21/02*    (2006.01)

(52) U.S. Cl.
    CPC .................... *C12P 21/02* (2013.01)

(58) Field of Classification Search
    CPC ........................................ C12P 21/02
    See application file for complete search history.

(56) References Cited

U.S. PATENT DOCUMENTS

| | | |
|---|---|---|
| 4,456,591 A | 6/1984 | Thomas |
| 4,749,780 A | 6/1988 | Andersson et al. |
| 4,784,950 A | 11/1988 | Hagen et al. |
| 4,868,112 A | 9/1989 | Toole, Jr. |
| 4,877,614 A | 10/1989 | Andersson et al. |
| 5,171,844 A | 12/1992 | van Ooyen et al. |
| 5,200,510 A | 4/1993 | Kumar et al. |
| 5,250,421 A | 10/1993 | Kaufman et al. |
| 5,422,260 A | 6/1995 | Kaufman et al. |
| 5,580,560 A | 12/1996 | Nicolaisen et al. |
| 5,661,008 A | 8/1997 | Almstedt et al. |
| 5,854,021 A | 12/1998 | Cho et al. |
| 5,997,864 A | 12/1999 | Hart et al. |
| 6,100,050 A | 8/2000 | Hemker et al. |
| 6,100,061 A | 8/2000 | Reiter et al. |
| 6,114,146 A | 9/2000 | Herlitschka et al. |
| 6,171,825 B1 | 1/2001 | Chan et al. |
| 6,307,032 B1 | 10/2001 | Schonhofer et al. |
| 6,358,703 B1 | 3/2002 | Cho et al. |
| 6,586,573 B1 | 7/2003 | Besman et al. |
| 6,599,724 B1 | 7/2003 | Mikaelsson et al. |
| 6,936,441 B2 | 8/2005 | Reiter et al. |
| 2003/0096366 A1* | 5/2003 | Knudsen ............ 435/69.1 |
| 2005/0266528 A1 | 12/2005 | Laemmie et al. |
| 2007/0212770 A1 | 9/2007 | Grillberger et al. |
| 2007/0219135 A1 | 9/2007 | Rojkjaer |

FOREIGN PATENT DOCUMENTS

| | | |
|---|---|---|
| JP | 2001061479 | 3/2001 |
| WO | WO-91/06314 | 5/1991 |
| WO | WO-91/09122 | 6/1991 |
| WO | WO-92/09698 | 6/1992 |
| WO | WO-92/15686 | 9/1992 |
| WO | WO-94/07510 | 4/1994 |
| WO | WO-99/20767 | 4/1999 |
| WO | WO-01/36664 | 5/2001 |
| WO | WO-01/58935 | 8/2001 |
| WO | WO-01/83725 | 11/2001 |
| WO | WO-02/22776 | 3/2002 |
| WO | WO-02/38162 | 5/2002 |
| WO | WO-02/077218 | 10/2002 |
| WO | WO-03/027147 | 4/2003 |
| WO | WO-03/037932 | 5/2003 |
| WO | WO-2008/141824 | 11/2008 |

OTHER PUBLICATIONS

Furukawa et al. Effect of culture temperature on a recombinant CHO cell line producing a Cterminal alpha-amidating enzyme. Cytotechnology 26: 153-164, 1998.*

Carvell et al. On-line measurements and control of viable cell density in cell culture manufacturing processes using radio-frequency impedance. Cytotechnology (2006) 50:35-48.*

Hansen et al. Influence of Ammonium on Growth, Metabolism, and Productivity of a Continuous Suspension Chinese Hamster Ovary Cell Culture. Biotechnol. hog. 1994, 70, 121-124.*

Chen et al. Temperature Shift as a Process Optimization Step for the Production of Pro-urokinase by a Recombinant Chinese Hamster Ovary Cell Line in High-Density Perfusion Culture. Journal of Bioscience and Bioengineering vol. 97, No. 4, 239-243. 2004.*

Gray et al. CO2 in large-scale and high-density CIIO cell perfusion culture. Cytotechnology 22: 65-78, 1996.*

Cooper et al. The Bulk Growth of Animal Cells in Continuous Suspension Culture. (1959). J. Gen. Microbiol. 21, 702-720.*

(Continued)

*Primary Examiner* — Taeyoon Kim

(74) *Attorney, Agent, or Firm* — Morgan, Lewis & Bockius LLP

(57) ABSTRACT

Culturing heterologous protein-secreting mammalian cells, such as CHO or BHK cells, at 35.1-36.5° C. and/or at pH 7.15-7.20 and/or at a dissolved $CO_2$ concentration of 10% or lower. Preferred heterologous proteins are Factor VIII, ADAMTS-13, furin or Factor VII.

26 Claims, No Drawings

(56) References Cited

OTHER PUBLICATIONS

Bachinger et al., Monitoring cellular state transitions in production-scale CHO-cell process using an electric nose. *J. Biotech.* 76(1): 61-71 (2000).
Cannizzaro et al., On-Line biomass monitoring of CHO perfusion culture with scanning dielectric spectroscopy. *Biotech. Bioeng.* 84(5): 597-610 (2003).
Daveys et al., From concept to market in industrial impedance applications. *Ann. NY Acad. Sci.* 873: 239-44 (1999).
Gomperts et al., The manufacturing process of recombinant factor VIII, recombinate. *Transfusion Med. Rev.* 6(4): 247-51 (1992).
Joeris et al., In-situ microscopy: Online process monitoring of mammalian cell cultures. *Cytotechnol.* 38(1-3): 129-34 (2002).
Kimura et al., Effects of elevated pCO2 and/or osmolality on the growth and recombinant tPA production of CHO cells. *Biotechnol. Bioeng.* 52(1): 152-160 (1996).
Konstantinov et al., Real-time biomass-concentration monitoring in animal-cell cultures. *Trends Biotechnol.* 12(8): 324-33 (1994).
Zhu et al., Effects of elevated pCO2 and osmolality on growth of CHO cells and production of antibody-fusion protein B1: a case study. *Biotech. Progress*, 21(1): 70-7 (2005).
International Search Report, PCT/US2008/08836, European Patent Office, dated Jul. 14, 2009.
Anderson et al., "Activation of the furin endoprotease is a multiple-step process: requirements for acidification and internal propeptide cleavage", *EMBO J.*, 16:1508-18 (1997).
Better et al., "*Escherichia coli* secretion of an active chimeric antibody fragment", *Science*, 240:1041-3 (1988).
Bird et al., "Single-chain antigen-binding proteins", *Science*, 242:423-6 (1988).
Bresnahan et al., "Human fur gene encodes a yeast KEX2-like endoprotease that cleaves pro-beta-NGF in vivo", *J. Cell Biol.*, 111:2851-9 (1990).
Creemers et al., "Modulation of furin-mediated proprotein processing activity by site-directed mutagenesis", *J. Biol. Chem.*, 268:21826-34 (1993).
Fox et al., "Maximizing interferon-gamma production by chinese hamster ovary cells through temperature shift optimization: experimental and modeling", *Biotechnol. Bioeng.*, 85:177-84 (2004).
Fujikawa et al., "Purification of human von Willebrand factor-cleaving protease and its identification as a new member of the metalloproteinase family", *Blood*, 98:1662-6 (2001).
Gerritsen et al., "Assay of von Willebrand factor (vWF)-cleaving protease based on decreased collagen binding affinity of degraded vWF: a tool for the diagnosis of thrombotic thrombocytopenic purpura (TTP)", *Thromb. Haemost.*, 82:1386-9 (1999).
Graham et al., "Characteristics of a human cell line transformed by DNA from human adenovirus type 5", *J. Gen. Virol.*, 36:59-74 (1977).
Hatsuzawa et al., "Molecular and enzymatic properties of furin, a Kex2-like endoprotease involved in precursor cleavage at Arg-X-Lys/Arg-Arg sites", *J. Biochem.*, 111:296-301 (1992).
Hatsuzawa et al., "Purification and characterization of furin, a Kex2-like processing endoprotease, produced in Chinese hamster ovary cells", *J. Biol. Chem.*, 267:16094-9 (1992).
Hedner et al., "Use of human factor VIIa in the treatment of two hemophilia A patients with high-titer inhibitors", *J. Clin. Invest.*, 71:1836-41 (1983).
Holst et al., "Local application of recombinant active-site inhibited human clotting factor VIIa reduces thrombus weight and improves patency in a rabbit venous thrombosis model", *Eur. J. Vasc. Endovasc. Surg.*, 15:515-20 (1998).
Hosaka et al., "Arg-X-Lys/Arg-Arg motif as a signal for precursor cleavage catalyzed by furin within the constitutive secretory pathway", *J. Biol. Chem.*, 266:12127-30 (1991).
Hu et al., "Large-scale mammalian cell culture", *Current Opinion in Biotechnology*, 8:148-53 (1997).

Huston et al., "Protein engineering of antibody binding sites: recovery of specific activity in an anti-digoxin single-chain Fv analogue produced in *Escherichia coli*", *Proc. Natl. Acad. Sci. USA*, 85:5879-83 (1988).
Iino et al., "Functional consequences of mutations in Ser-52 and Ser-60 in human blood coagulation factor VII", *Arch. Biochem. Biophys.*, 352:182-92 (1998).
Kaufman et al., "Effect of von Willebrand factor coexpression on the synthesis and secretion of factor VIII in Chinese hamster ovary cells", *Mol. Cell Biol.*, 9:1233-42 (1989).
Kazama et al., "Hepsin, a putative membrane-associated serine protease, activates human factor VII and initiates a pathway of blood coagulation on the cell surface leading to thrombin formation", *J. Biol. Chem.*, 270:66-72 (1995).
Kornfelt et al., "Oxidation of methionine residues in coagulation factor VIIa", *Arch. Biochem. Biophys.*, 363:43-54 (1999).
Kumar et al., "Proliferation control strategies to improve productivity and survival during CHO based production culture", *Cytotechnol.*, 53:33-46 (2007).
Lara et al., "Living with heterogeneities in bioreactors", *Mol. Biotechnol.*, 34:355-81 (2006).
Leduc et al., "Activation of human furin precursor processing endoprotease occurs by an intramolecular autoproteolytic cleavage", *J. Biol. Chem.*, 267:14304-8 (1992).
Lind et al., "Novel forms of B-domain-deleted recombinant factor VIII molecules. Construction and biochemical characterization", *Eur. J. Biochem.*, 232:19-27 (1995).
Mather et al., "Culture of testicular cells in hormone-supplemented serum-free medium", *Ann NY Acad. Sci.*, 383:44-68 (1982).
Mather, "Establishment and characterization of two distinct mouse testicular epithelial cell lines", *Biol. Reprod.*, 23:243-51 (1980).
Mollerup et al., "The use of RP-HPLC for measuring activation and cleavage of rFVIIa during purification", *Biotechnol. Bioeng.*, 48:501-5 (1995).
Molloy et al., "Human furin is a calcium-dependent serine endoprotease that recognizes the sequence Arg-X-X-Arg and efficiently cleaves anthrax toxin protective antigen", *J. Biol. Chem.*, 267:16396-402 (1992).
Morrison et al., "Chimeric human antibody molecules: mouse antigen-binding domains with human constant region domains", *Proc. Natl. Acad. Sci. USA*, 81:6851-5 (1984).
Nicolaisen et al., "FVIIa derivatives obtained by autolytic and controlled cathepsin G mediated cleavage", *FEBS Lett.*, 317:245-9 (1993).
Osterud et al., "Activation of the coagulation factor VII by tissue thromboplastin and calcium", *Biochemistry*, 11:2853-7 (1972).
Pattison et al., "Measurement and control of dissolved carbon dioxide in mammalian cell culture processes using an in situ fiber optic chemical sensor", *Biotechnol. Prog.*, 16:769-74 (2000).
Persson et al., "Ca2+ binding to the first epidermal growth factor-like domain of factor VIIa increases amidolytic activity and tissue factor affinity", *J. Biol. Chem.*, 272:19919-24 (1997).
Persson, "Characterization of the interaction between the light chain of factor VIIa and tissue factor", *FEBS Lett.*, 413:359-63 (1997).
Plaimauer et al., "'Shed' furin: mapping of the cleavage determinants and identification of its C-terminus", *Biochem. J.*, 354:689-95 (2001).
Plaimauer et al., "Cloning, expression, and functional characterization of the von Willebrand factor-cleaving protease (ADAMTS13)", *Blood*, 100:3626-3632 (2002).
Plaimauer et al., "Expression and characterization of recombinant human ADAMTS-13", *Semin. Hematol.*, 41:24-33 (2004).
Rehemtulla et al., "Preferred sequence requirements for cleavage of pro-von Willebrand factor by propeptide-processing enzymes", *Blood*, 79:2349-55 (1992).
Rieger et al., "Relation between ADAMTS13 activity and ADAMTS13 antigen levels in healthy donors and patients with thrombotic microangiopathies (TMA)", *Thromb. Haemost.*, 95:212-20 (2006).
Schlokat et al., "Large scale production of recombinant von Willebrand factor", *Thromb. Haemost.*, 78:1160 (1995).

(56) References Cited

OTHER PUBLICATIONS

Schlokat et al., "Production of highly homogeneous and structurally intact recombinant von Willebrand factor multimers by furin-mediated propeptide removal in vitro", *Biotechnol. Appl. Biochemistry*, 24:257-67 (1996).

Skerra et al., "Assembly of a functional immunoglobulin Fv fragment in *Escherichia coli*", *Science*, 240:1038-41 (1988).

Teuchert et al., "Sorting of furin at the trans-Golgi network. Interaction of the cytoplasmic tail sorting signals with AP-1 Golgi-specific assembly proteins", *J. Biol. Chem.*, 274:8199-207 (1999).

Thim et al., "Amino acid sequence and posttranslational modifications of human factor VIIa from plasma and transfected baby hamster kidney cells", *Biochemistry*, 27:7785-93 (1998).

Tripodi et al., "Second international collaborative study evaluating performance characteristics of methods measuring the von Willebrand factor cleaving protease (ADAMTS-13)", *J. Thromb. Haemost.*, 6:1534-41 (2008).

Trummer et al., "Process parameter shifting: part I. Effect of DOT, pH, and temperature on the performance of Epo-Fc expressing CHO cells cultivated in controlled batch bioreactors", *Biotechnol. Bioeng.*, 94:1033-44 (2006).

Urlaub et al., "Isolation of Chinese hamster cell mutants deficient in dihydrofolate reductase activity", *Proc. Natl. Acad. Sci. USA*, 77:4216-20 (1980).

Van De Ven et al., "Structure and function of eukaryotic proprotein processing enzymes of the subtilisin family of serine proteases", *Crit. Rev. Oncog.*, 4:115-36 (1993).

Vey et al., "Maturation of the trans-Golgi network protease furin: compartmentalization of propeptide removal, substrate cleavage, and COOH-terminal truncation", *J. Cell. Biol.*, 127:1829-42 (1994).

Vidricaire et al., "Characterization of a secreted form of human furin endoprotease", *Biochem. Biophys. Res. Commun.*, 195:1011-8 (1993).

Wakabayashi et al., "Conformation-specific monoclonal antibodies to the calcium-induced structure of protein C", *J. Biol. Chem.*, 11097-105 (1986).

Ward et al., "Binding activities of a repertoire of single immunoglobulin variable domains secreted from *Escherichia coli*", *Nature*, 341:544-6 (1989).

Wasley et al., "PACE/furin can process the vitamin K-dependent pro-factor IX precursor within the secretory pathway", *J. Biol. Chem.*, 268:8458-65 (1993).

Wildgoose et al., "Synthesis, purification, and characterization of an Arg152—Glu site-directed mutant of recombinant human blood clotting factor VII", *Biochemistry*, 29:3413-20 (1990).

Wise et al., "Expression of a human proprotein processing enzyme: correct cleavage of the von Willebrand factor precursor at a paired basic amino acid site", *Proc. Natl. Acad. Sci. USA*, 87:9378-82 (1990).

Wood et al., "Expression of active human factor VIII from recombinant DNA clones", *Nature*, 312:330-7 (1984).

Partial International Search Report for counterpart International Application No. PCT/US08/88036 (Apr. 23, 2009).

\* cited by examiner

CELL CULTURE PROCESSES

This application claims priority of U.S. Provisional Application No. 61/009,328, filed Dec. 27, 2007, which is incorporated by reference herein in its entirety.

FIELD OF THE INVENTION

The invention relates to processes for culturing mammalian cells, particularly mammalian cells that secrete heterologous and/or recombinant proteins and, more particularly, mammalian cells that secrete blood proteins, such as blood clotting factor VIII (hereinafter 'Factor VIII', or just 'FVIII'), ADAMTS-13, furin or clotting factor VII (hereinafter 'Factor VII', or just 'FVII').

BACKGROUND OF THE INVENTION

Blood clotting Factor VIII is a trace plasma glycoprotein that is found in mammals and is involved as a cofactor of IXa in the activation of Factor X. An inherited deficiency of Factor VIII results in the bleeding disorder haemophilia A, which can be treated successfully with purified Factor VIII. The Factor VIII can be extracted from blood plasma or can be produced by recombinant-DNA-based techniques. In the plasma, it circulates as a complex with von Willebrand Factor (vWF).

Recombinant Factor VIII (rFVIII) can be produced by Chinese Hamster Ovary (CHO) cells transfected with a vector carrying a DNA sequence encoding the Factor VIII molecule. In some cases, recombinant Factor VIII is co-produced with recombinant von Willebrand Factor (rvWF), which stabilises the Factor VIII. Such co-production can involve the co-culturing of respective cell lines that express FVIII and vWF, or the co-expression of the two proteins in the same cell. See U.S. Pat. No. 5,250,421 (Genetics Institute) and Kaufman et al (1989) *Mol. Cell. Biol.* 9, 1233-1242.

In a typical process for preparing recombinant Factor VIII, cells are cultured in a medium and secrete Factor VIII into the medium. Factor FVIII may then be purified from the medium, optionally as a complex with vWF.

Recombinant Factor VIII is expensive to produce due to the relatively low yields obtained in processes known in the art. The yield per cell tends to be low compared to the yield that might be obtained for other recombinant proteins. If the culture medium is not supplemented with animal products, such as serum, the medium may support only relatively low cell densities. This reduces the yield per volume of medium. However, it is desirable not to supplement the culture medium with animal products in order to reduce the risk of contamination with viruses and other transmissible agents. Animal-protein-free media for the production of FVIII are known from U.S. Pat. No. 6,936,441 (Baxter AG), for example.

The present invention provides processes for producing blood proteins, including rFVIII, in which the yield is improved compared to processes known in the art.

SUMMARY OF THE INVENTION

A first aspect of the invention provides a method of culturing heterologous protein-secreting mammalian cells in a cell culture supernatant wherein the cell culture supernatant is maintained at a temperature that is set at X±0.9° C. wherein X has a value of from 35.1 to 36.5, with the proviso that the temperature is set at less than 37° C.

A second aspect of the invention provides a method of culturing heterologous protein-secreting mammalian cells in a cell culture supernatant wherein the cell culture supernatant is maintained at a pH that is set at X±0.05 wherein X has a value of from 7.15 to 7.20, with the proviso that the pH is set at greater than 7.10.

A third aspect of the invention provides a method of culturing heterologous protein-secreting mammalian cells in a cell culture supernatant wherein the cell culture supernatant has a $CO_2$ concentration of 1-10%.

A fourth aspect of the invention provides a method of continuous culture of FVIII-secreting mammalian cells in a vessel comprising a cell culture supernatant wherein the density of the cells in the cell culture supernatant is measured by an in-line sensor and the influx of fresh medium into the vessel is automatically controlled so as to maintain the density of the cells in a desired range.

DETAILED DESCRIPTION OF PREFERRED EMBODIMENTS OF THE INVENTION

In the process of the first aspect of the invention, the cell culture supernatant in which the mammalian cells are cultured is maintained at a temperature that is set at X±0.9° C. wherein X has a value of from 35.1 to 36.5, with the proviso that the temperature is set at less than 37° C. In preferred embodiments, the temperature is set at 36±0.9° C., preferably 36±0.5° C., more preferably 36±0.2° C. and most preferably 36° C.; or 35.1±0.9° C., preferably 35.1±0.5° C., more preferably 35.1±0.2° C. and most preferably 35.1° C.; or 36.5±0.9° C., 36.5±0.5° C., more preferably 36.5±0.2° C. and most preferably 36.5° C.

The "cell culture supernatant" is the medium in which the mammalian cells are cultured. This medium is not to be confused with feed medium that may be added to the culture, although feed medium is also preferably added to the culture at the temperature at which the cell culture supernatant is set. By "culture" we mean the cell culture supernatant and the mammalian cells cultured therein. Conventionally, mammalian cells are cultured at 37° C. Surprisingly, the applicant has found that culturing the mammalian cells at a lower temperature, such as 36° C. increases the yield of recombinant protein.

By "culturing at" or "maintaining at" a temperature, we refer to the temperature to which the process control systems are set, in other words the intended, target, temperature. Clearly, there will be small variations of the temperature of a culture over time, and from location to location through the culture vessel. Where we refer to "culturing at" or "maintaining at" a temperature that is set at X±Y ° C., we mean that the set point is at a value of from X+Y ° C. to X−Y ° C. So, for example where X is 36.01±0.9° C., the set-point is set at a value of from 35.1 to 36.9. For each of the preferred values of X, the set-point is at a value within the range X±0.9° C., 0.8° C., ±0.7° C., ±0.6° C., ±0.5° C., ±0.4° C., ±0.3° C., ±0.2° C., or ±0.1° C. Narrower ranges are preferred. A set-point of X is most preferred.

For any given set-point, slight variations in temperature may occur. Typically, such variation may occur because heating and cooling elements are only activated after the temperature has deviated somewhat from the set-point. In that case, the set-point is X(±Y) and the heating or cooling element is activated when the temperature varies by ±Z ° C., as appropriate. Typically, the permissible degree of deviation of the temperature from the set-point before heating or cooling elements are activated may be programmed in the process control system. Temperature may be controlled to the nearest ±0.5° C., ±0.4° C., ±0.3° C., ±0.2° C. or even ±0.1° C. by heating and cooling elements controlled by thermostats.

Larger differentials in temperature may also be programmed, such as ±0.9° C., ±0.8° C., ±0.7° C. or ±0.6° C. The temperature may also be controlled by immersion of the culture vessel in a heating bath at a particular temperature. Conceivably, there is no variation from the set-point because the heating is applied continually. Another source of variation arises due to measurement error in the temperature of the cell culture supernatant. Typical thermometers used in cell culture equipment may have a variability of ±0.3° C. or ±0.2° C., or even ±0.1° C.

Where the set-point is set at a value within the range X±Y ° C., and the tolerance of the temperature is ±Z ° C. (i.e. a heater or cooler is activated when the temperature deviates by ±Z ° C., as appropriate) this can also be expressed as a set-point of (X−Y to X+Y) ±Z ° C. For each possible value of X, all combinations of Y ° C. and ±Z ° C., as indicated above, are envisaged, with the proviso that the temperature is set at less than 37° C.

In one preferred embodiment, the temperature is set at 36±Y° C. Preferably, the temperature is set at (35.4-36.6) ±0.3° C., ±0.2° C., ±0.1° C. or ±0; or (35.5-36.5) ±0.4° C., ±0.3° C., ±0.2° C., 0.1° C. or ±0; or (35.6-36.4) ±0.5° C., ±0.4° C., ±0.3° C., ±0.2° C., ±0.1° C. or ±0; or (35.7-36.3) ±0.6° C., ±0.5° C., ±0.4° C., ±0.3° C., ±0.2° C., ±0.1° C. or ±0; or (35.8-36.2) ±0.7° C., ±0.6° C., ±0.5° C., ±0.4° C., ±0.3° C., ±0.2° C., ±0.1° C. or ±0; or (35.9-36.1) ±0.8° C., ±0.7° C., ±0.6° C., ±0.5° C., ±0.4° C., ±0.3° C., ±0.2° C., 0.1° C. or ho; or 36±0.9° C., ±0.8° C., 0.7° C., ±0.6° C., ±0.5° C., ±0.4° C., ±0.3° C., ±0.2° C., ±0.1° C. or ±0° C.

In another preferred embodiment, the temperature is set at 35.11±Y° C. Preferably, the temperature is set at (34.5-35.7) ±0.3° C., ±0.2° C., ±0.1° C. or ±0; or (34.6-35.6) ±0.4° C., ±0.3° C., ±0.2° C., ±0.1° C. or ±0; or (34.7-35.5) ±0.5° C., ±0.4° C., ±0.3° C., ±0.2° C., 0.1° C. or ±0; or (34.8-35.4) ±0.6° C., ±0.5° C., ±0.4° C., ±0.3° C., ±0.2° C., ±0.1° C. or ±0; or (34.9-35.3) ±0.7° C., ±0.6° C., ±0.5° C., ±0.4° C., ±0.3° C., ±0.2° C., ±0.1° C. or ±0; or (35.0-35.2) ±0.8° C., ±0.7° C., ±0.6° C., ±0.5° C., ±0.4° C., ±0.3° C., ±0.2° C., ±0.1° C. or ±0; or 35.1±0.9° C., ±0.8° C., ±0.7° C., ±0.6° C., ±0.5° C., ±0.4° C., ±0.3° C., ±0.2° C., ±0.1° C. or ±0° C.

In another preferred embodiment, the temperature is set at 36.5±Y° C. Preferably, the temperature is set at (36.1-36.9) ±0; or (36.2-36.8)±0.1° C. or ±0; or (36.3-36.7) ±0.2° C., ±0.1° C. or ±0; or (36.4-36.6) ±0.3° C., ±0.2° C., ±0.1° C. or ±0; or 36.5±0.4° C., ±0.3° C., ±0.2° C., ±0.1° C. or 0.

In the process of the second aspect of the invention, the cell culture supernatant is maintained at a pH that is set at X±0.05 wherein X has a value of from 7.15 to 7.20, with the proviso that the pH is set at greater than 7.10. In preferred embodiments, the pH is set at 7.20±0.05, preferably 7.20±0.03, more preferably 7.20±0.01 and most preferably at 7.20; or 7.15±0.05, preferably 7.15±0.03, more preferably 7.15±0.01 and most preferably at 7.15. In a conventional process for producing a recombinant protein, the cell culture supernatant is maintained at pH 7.1. Surprisingly, the applicant has found that culturing the mammalian cells at a higher pH, such as pH 7.2 increases the yield of recombinant protein.

By "culturing at" or "maintaining at" a pH, we refer to the pH to which the process control systems are set, in other words the intended, target, pH. Where we refer to "culturing at" or "maintaining at" a pH that is set at X±Y, we mean that the set point is at a value of from X+Y to X−Y. For each of the preferred values of X, the set-point is at a value within the range X±0.05, ±0.04, ±0.03, ±0.02 or ±0.01. Narrower ranges are preferred. A set-point of X is most preferred.

For any given set-point, slight variations in pH may occur. Typically, such variation may occur because means which control pH, for example by adding acid or base, or changing the sparge rate, are only activated after the pH has deviated somewhat from the set-point. Typically, the pH is controlled to the nearest ±0.05, ±0.04, ±0.03, ±0.02 or ±0.01 units of pH.

Where the pH set-point is set at a value within the range X±Y, and the tolerance is ±Z, this can also be expressed as a set-point of (X−Y to X+Y) ±Z. For each possible value of X, all combinations of ±Y and ±Z, as indicated above, are envisaged, with the proviso that the pH is set at greater than 7.10.

In one preferred embodiment, the pH is set at 7.20±Y. Preferably, the pH is set at (7.15-7.25) ±0; or (7.16-7.24) ±0.1 or ±0; or (7.17-7.23) ±0.2, ±0.1 or ±0; or (7.18-7.22) ±0.3, ±0.2, ±0.1 or ±0; or (7.19-7.21) ±0.4, ±0.3, ±0.2, ±0.1 or ±0; or 7.20±0.5, ±0.4, ±0.3, ±0.2, ±0.1 or ±0.

In another preferred embodiment, the pH is set at 7.15±Y. Preferably, the pH is set at (7.11-7.19) 0; or (7.12-7.18) ±0.1 or ±0; or (7.13-7.17) ±0.2, ±0.1 or ±0; or (7.14-7.16) ±0.3, ±0.2, ±0.1 or ±0; or 7.15±0.4, ±0.3, ±0.2, ±0.1 or ±0.

In the process of the third aspect of the invention, the cell culture supernatant has a $CO_2$ concentration of 1 to 10%, for example 4.0-9.0%, 5.5-8.5% or about 6-8%. Conventionally, $CO_2$ concentration is higher than this due to the $CO_2$ produced by the cells not being removed from the cell culture supernatant. Surprisingly, the applicant has found that maintaining the $CO_2$ concentration at 10% or lower increases the yield of recombinant protein. It helps the $dCO_2$ to be kept low if the feed medium is degassed (for example by bubbling air through it) as well as the cell culture supernatant in the bioreactor being sparged.

Preferably, the process of each of the first three aspects of the invention is operated to include the particular feature specified in relation to the process of one or more of the other aspects of the invention. In other words, where the temperature is maintained at X±0.9° C., wherein X has a value of from 35.1 to 36.5° C., it is advantageous to also maintain the pH at X±0.05 wherein X has a value of from 7.15 to 7.20, and/or the $CO_2$ concentration at 10% or lower. Where the pH is maintained at X±0.05 wherein X has a value of from 7.15 to 7.20, it is advantageous also to maintain the temperature at X±0.9° C., wherein X has a value of from 35.1 to 36.5° C., and/or the $CO_2$ concentration at 10% or lower. Where the $CO_2$ concentration is maintained at 10% or lower, it is advantageous also to maintain the pH at X±0.05 wherein X has a value of from 7.15 to 7.20, and/or the temperature at X±0.9° C., wherein X has a value of from 35.1 to 36.5° C.

Ways of monitoring the three defined parameters (temperature, pH and $CO_2$ concentration) are well known in this art and generally rely on probes that are inserted into the bioreactor, or included in loops through which the culture medium is circulated, or inserted into extracted samples of culture medium. A suitable in-line $dCO_2$ sensor and its use are described in Pattison et al (2000) *Biotechnol. Prog.* 16:769-774. A suitable in-line pH sensor is Mettler Toledo InPro 3100/125/Pt100 (Mettler-Toledo Ingold, Inc., Bedford, Mass.). A suitable off-line system for measuring $dCO_2$, in addition to pH and pO2 is the BioProfile pHOx (Nova Biomedical Corporation, Waltham Mass.). In this system, $dCO_2$ is measured by potentiometric electrodes within the range 3-200 mmHg with an imprecision resolution of 5%. pH may be measured in this system at a temperature of 37° C., which is close to the temperature of the cell culture supernatant in the bioreactor. Ways of altering the specified parameter in order to keep it at the predefined level are also well known. For example, keeping the temperature constant usually involves heating or cooling the bioreactor or the feed medium (if it is a fed-batch or continuous process); keeping the pH constant usually involves choosing and supplying enough of an appropriate buffer (typically bicarbonate) and adding acid, such as hydrochloric acid, or alkali, such as sodium hydroxide, sodium bicarbonate or a mixture thereof, to the feed medium as necessary; and keeping the $CO_2$ concentration constant usually involves adjusting the sparging rate (see further below), or regulating the flow of $CO_2$ in the head space. It is possible that the calibration of an in-line pH probe may drift over time, such as over periods of days or weeks, during which the cells are cultured. In that event, it may be beneficial to reset the in-line probe by using measurements obtained from a recently calibrated off-line probe. A suitable off-line probe is the BioProfile pHOx (Nova Biomedical Corporation, Waltham Mass.).

The inventors have found that increasing pH (e.g. by adding NaOH) is not enough on its own to achieve the maximum benefit in terms of the production of active protein. Instead, it is desirable to reduce the $CO_2$ concentration. Normally, one would keep the other parameters of the process constant. However, the inventors have found that it is advantageous to reduce the $CO_2$ concentration but to allow the pH to rise from 7.1, for example to 7.15 or 7.2, preferably without adding NaOH.

Mammalian cell cultures need oxygen for the cells to grow. Normally, this is provided by forcing oxygen into the culture through injection ports. It is also necessary to remove the $CO_2$ that accumulates due to the respiration of the cells. This is achieved by 'sparging', i.e., passing a gas through the bioreactor in order to entrain and flush out the $CO_2$. Conventionally, this can also be done using oxygen. However, the inventors have found that it is advantageous to use air instead. It has been found that usually a conventional inert gas such as nitrogen is less effective at sparging $CO_2$ than using air. Given that air is about 20% oxygen, one might have thought that five times as much air would be used. However, this has been found to be inadequate in large scale cultures, particularly in cultures at 2500 L scale. In a 2500 L bioreactor, 7 to 10 times as much air, preferably about 9 times as much air, is used. For example, under standard conditions, the 2500 L bioreactor is sparged with $O_2$ at a 10 µm bubble size at a rate of 0.02 VVH (volume $O_2$ per volume of culture per hour). The same 2500 L bioreactor used according to the method of the invention would be sparged with air at a 10 µm bubble size at a rate of 0.18 VVH.

Hence, the use of surprisingly high volumes of air has been found to provide adequate oxygen supply and to remove the unwanted $CO_2$.

During production phase, it is preferred to remove $CO_2$ by air sparging, as described above. This is especially the case when using bioreactors of large capacity, in which the cell culture supernatant would otherwise accumulate $CO_2$ to deleteriously high levels. However, at the beginning of culture, or in small scale culture, such as at 1 L or 2.5 L scale, the head space may be overlayed with $CO_2$. Under such conditions, low levels of $dCO_2$ may still be achieved. Overlaying the headspace with $CO_2$ may also be used to reduce the pH to the set-point, if the pH is too basic.

The cells may be any mammalian cell that can be cultured, preferably in a manufacturing process (i.e. at least 1 liter), to produce a desired protein such as FVIII. Examples include the monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 [1977]); baby hamster kidney cells (BHK, ATCC CCL 10); Chinese hamster ovary cells/−DHFR, such as the DUKX-B11 subclone (CHO, Urlaub and Chasin, *Proc. Natl. Acad. Sci. USA*, 77:4216 [1980]); mouse sertoli cells (TM4, Mather, *Biol. Reprod.*, 23:243-251 [1980]); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 [1982]); MRC 5 cells; FS4 cells; and the human hepatoma line (Hep G2). Preferably, the cell line is a rodent cell line, especially a hamster cell line such as CHO or BHK.

A preferred method of preparing stable CHO cell clones expressing a recombinant protein is as follows. A DHFR deficient CHO cell line DUKX-BII is transfected with a DHFR expression vector to allow for expression of the relevant recombinant protein, essentially as described in U.S. Pat. No. 5,250,421 (Kaufman et al, Genetics Institute, Inc.) Transfection is selected for with methotrexate. Amplification of the relevant region coding for expression of the recombinant protein and DHFR gene is achieved by propagation of the cells in increasing concentrations of methotrexate. Where appropriate, CHO cell lines may be adapted for growth in serum and/or protein free medium, essentially as described in U.S. Pat. No. 6,100,061 (Reiter et al, Immuno Aktiengesellschaft)

The basal medium chosen for culturing the host cell line is not critical to the present invention and may be any one of, or combination of, those known to the art which are suitable for culturing mammalian cells. Media such as Dulbecco's Modified Eagle Medium, Ham's F-12 Medium, Eagle's Minimal Essential Medium and RPMI-1640 Medium and the like are commercially available. The addition of growth factors such as recombinant insulin is optional.

Historically, animal cells have been cultured in media containing animal serum. However, such media are incompletely defined and carry the risk of infection. Those in the art have therefore devised "protein-free" media that are either completely free of any protein or at least are free of any protein that is not recombinantly produced. Due to the labile nature of Factor VIII, the productivity of the engineered host cells is severely reduced under protein-free conditions. Human serum albumin is commonly used as a serum-free culture supplement for the production of recombinant proteins. The albumin itself stabilizes the FVIII and the impurities present in serum-derived albumin preparations may also contribute to the stabilizing effect of albumin. Factors such as lipoprotein have been identified as a replacement for human serum albumin for the production of recombinant Factor VIII under serum-free conditions.

Preferred media include those disclosed in U.S. Pat. No. 6,171,825 (Bayer, Inc) and U.S. Pat. No. 6,936,441 (Baxter AG).

The medium of U.S. Pat. No. 6,171,825 consists of modified Dulbecco's Minimum Essential Medium and Ham's F-12 Medium (50:50, by weight) supplemented with recombinant insulin, iron, a polyol, copper and optionally other trace metals.

The insulin should be recombinant and can be obtained as 'Nucellin' insulin from Eli Lilly). It can be added at 0.1 to 20 µg/ml (preferably 5-15 µg/ml, or about 10 µg/ml). The iron is preferably in the form of $Fe^{2+}$ ions, for example provided as $FeSO_4$.EDTA, and can be present at 5-10 µM (preferably about 50 µm). Suitable polyols include non-ionic block copolymers of poly(oxyethylene) and poly(oxypropylene) having molecular weights ranging from about 1000 to about 16,000. A particularly preferred polyol is Pluronic F-68 (BASF Wyandotte), which has an average molecular weight of 8400 and consists of a centre block of poly(oxypropylene) (20% by weight) and blocks of poly(oxyethylene) at both ends. It is also available as Synperonic F-68 from Unichema Chemie BV. Others include Pluronics F-61, F-71 and F-108. Copper ($Cu^{2+}$) may be added in an amount equivalent to 50-800 nM $CuSO_4$, preferably 100-400 nM, conveniently about 250 nM. The inclusion of a panel of trace metals such as manganese, molybdenum, silicon, lithium and chromium can lead to further increases in Factor VIII production. BHK cells grow well in this protein-free basal medium.

The medium of U.S. Pat. No. 6,936,441 is also based on a 50/50 mixture of DMEM and Ham's F12 but includes soybean peptone or yeast extract at between 0.1 and 100 g/l, preferably between 1 and 5 g/l. As a particularly preferred embodiment, soybean extract, e.g. soybean peptone, may be used. The molecular weight of the soybean peptone can be less than 50 kD, preferably less than 10 kD. The addition of ultrafiltered soybean peptone having an average molecular weight of 350 Dalton has proven particularly advantageous for the productivity of the recombinant cell lines. It is a soybean isolate having a total nitrogen content of about 9.5% and a free amino acid content of about 13%, or about 7-10%.

A particularly preferred medium has the following composition: synthetic minimum medium (e.g. 50/50 DMEM/Ham's F12) 1 to 25 g/l; soybean peptone 0.5 to 50 g/l; L-glutamine 0.05 to 1 g/l; $NaHCO_3$ 0.1 to 10 g/l; ascorbic acid 0.0005 to 0.05 g/l; ethanolamine 0.0005 to 0.05; and sodium selenite 1 to 15 µg/l. Optionally, a non-ionic surface-active agent such as a polypropylene glycol (e.g. Pluronic F-61, Pluronic F-68, Pluronic F-71 or Pluronic F-108) maybe added to the medium as a defoaming agent. This agent is generally applied to protect the cells from the negative effects of aeration ("sparging"), since without the addition of a surface-active agent the rising and bursting air bubbles may damage those cells that are at the surface of the air bubbles.

The amount of non-ionic surface-active agent may range between 0.05 and 10 g/l, preferably between 0.1 and 5 g/l. Furthermore, the medium may also contain cyclodextrine or a derivative thereof. Preferably, the serum- and protein-free medium contains a protease inhibitor, such as a serine protease inhibitor, which is suitable for tissue culture and which is of synthetic or vegetable origin.

In another preferred embodiment the following amino acid mixture is additionally added to the above-mentioned medium: L-asparagine (0.001 to 1 g/l; preferably 0.01 to 0.05 g/l; particularly preferably 0.015 to 0.03 g/l), L-cysteine (0.001 to 1 g/l; preferably 0.005 to 0.05 g/l; particularly preferably 0.01 to 0.03 g/l), L-cystine (0.001 to 1 g/l; preferably 0.01 to 0.05 g/l; particularly preferably 0.015 to 0.03 g/l), L-proline (0.001 to 1.5 g/l; preferably 0.01 to 0.07 g/l; particularly preferably 0.02 to 0.05 g/l), L-tryptophan (0.001 to 1 g/l; preferably 0.01 to 0.05 g/l; particularly preferably 0.015 to 0.03 g/l) and L-glutamine (0.05 to 10 g/l; preferably 0.1 to 1 g/l). These amino acids may be added to the medium individually or in combination. The combined addition of the amino acid mixture containing all of the above-mentioned amino acids is particularly preferred.

In a particular embodiment a serum- and protein-free medium is used additionally containing a combination of the above-mentioned amino acid mixtures and purified, ultrafiltered soybean peptone.

The medium of U.S. Pat. No. 6,936,441 is particularly well suited to the culturing of CHO cells but may be used with other cells as well.

A further suitable medium is the oligopeptide-free medium disclosed in US 2007/0212770 (Grillberger et al; Baxter International Inc., Baxter Healthcare S.A.)

Preferably, the culture medium is buffered by the use of bicarbonate ions, typically supplied as sodium bicarbonate.

Suitably, the culture medium has an osmolality of between 210 and 650 mOsm, preferably 270 to 450 mOsm, more preferably 310 to 350 mOsm and most preferably 320 mOsm. Preferably, the osmolality of the supernatant is maintained within one or more of these ranges throughout the method of the invention.

The culture can be any conventional type of culture, such as batch, fed-batch or continuous, but is preferably fed-batch or continuous. Suitable continuous cultures included repeated batch, chemostat, turbidostat or perfusion culture.

A batch culture starts with all the nutrients and cells that are needed, and the culture proceeds to completion, i.e. until the nutrients are exhausted or the culture is stopped for some reason.

A fed-batch culture is a batch process in the sense that it starts with the cells and nutrients but it is then fed with further nutrients in a controlled way in order to limit the growth of the cells. The fed-batch strategy is typically used in bio-industrial processes to reach a high cell density in the bioreactor. The feed solution is usually highly concentrated to avoid dilution of the bioreactor. The controlled addition of the nutrient directly affects the growth rate of the culture and allows one to avoid overflow metabolism (formation of metabolic by-products) and oxygen limitation (anaerobiosis). In most cases the growth-limiting nutrient is glucose which is fed to the culture as a highly concentrated glucose syrup (for example 600-850 g/l).

Different strategies can be used to control the growth in a fed-batch process. For example, any of dissolved oxygen tension (DOT, pO2), oxygen uptake rate (OUR), glucose concentration, lactate concentration, pH and ammonia concentration can be used to monitor and control the culture growth by keeping that parameter constant. In a continuous culture, nutrients are added and, typically, medium is extracted in order to remove unwanted by-products and maintain a steady state. Suitable continuous culture methods are repeated batch culture, chemostat, turbidostat and perfusion culture.

CHO cells, for example, may be cultured in a stirred tank or an airlift tank that is perfused with a suitable medium at a perfusion rate of from 2 to 10 volume exchanges per day and at an oxygen concentration of between 40% and 60%, preferably about 50%. Moreover, the cells may be cultured by means of the chemostat method, using the preferred pH value given above, an oxygen concentration of between 10% and 60% (preferably about 20%) and a dilution rate D of 0.25 to 1.0, preferably about 0.5.

In a repeated batch culture, also known as serial subculture, the cells are placed in a culture medium and grown to a desired cell density. To avoid the onset of a decline phase and cell death, the culture is diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state. Serial subculture is characterised in that the volume of culture is always increasing stepwise, there can be multiple harvests, the cells continue to grow and the process can continue for as long as desired.

In the chemostat and turbidostat methods, the extracted medium contains cells. Thus, the cells remaining in the cell culture vessel must grow to maintain a steady state. In the chemostat method, the growth rate is typically controlled by controlling the dilution rate i.e. the rate at which fresh medium is added. The cells are cultured at a sub-maximal growth rate, which is achieved by restricting the dilution rate. The growth rate is typically high. In contrast, in the turbidostat method, the dilution rate is set to permit the maximum growth rate that the cells can achieve at the given operating conditions, such as pH and temperature.

In a perfusion culture, the extracted medium is depleted of cells because most of the cells are retained in the culture vessel, for example by being retained on a membrane through which the extracted medium flows. However, typically such a membrane does not retain 100% of cells, and so a proportion are removed when the medium is extracted. It may not be crucial to operate perfusion cultures at very high growth rates, as the majority of the cells are retained in the culture vessel.

Continuous cultures, particularly repeated batch, chemostat and turbidostat cultures, are typically operated at high growth rates. According to common practice, it is typical to seek to maintain growth rates at maximum, or close to maximum, in an effort to obtain maximum volumetric productivity. Volumetric productivity is measured in units of protein quantity or activity per volume of culture per time interval. Higher cell growth equates to a higher volume of culture being produced per day and so is conventionally considered to reflect a higher volumetric productivity. The present inventors have unexpectedly found that, in certain embodiments, maximum volumetric productivity is not attained at the maximum growth rate of the cell. As described in the Examples, a maximum growth rate of a furin expressing CHO cell clone in chemostat culture was observed at a temperature of 36.5° C., but the maximum volumetric productivity was observed at 35.1° C. Despite the lower harvest volumes obtained, arising from a lower growth rate at the lower temperature, the amount of recombinant protein produced was so much greater that the lower temperature culture was, overall, the more productive.

Suitably, in any of the first, second or third aspects of the invention, the cell culture supernatant is maintained at a temperature that is set at a temperature which is lower than the temperature at which maximum growth rate is observed by at least 0.5° C., preferably at least 1.0° C. In this embodiment, it is preferred that the culture is a continuous culture, particularly a repeated batch, chemostat or turbidostat culture.

Mammalian cells such as CHO and BHK cells are generally cultured as suspension cultures. That is to say, the cells are suspended in the medium, rather than adhering to a solid support. The cells may alternatively be immobilized on a carrier, in particular on a microcarrier. Porous carriers, such as Cytoline®, Cytopore® or Cytodex®, may be particularly suitable.

The cell density is commonly monitored in cell cultures. In principle, a high cell density would be considered to be desirable since, provided that the productivity per cell is maintained, this should lead to a higher productivity per bioreactor volume. However, increasing the cell density can actually be harmful to the cells, and the productivity per cell is reduced. There is therefore a need to monitor cell density. To date, in mammalian cell culture processes, this has been done by extracting samples of the culture and analysing them under a microscope or using a cell counting device such as the CASY TT device sold by Schärfe System GmbH, Reutlingen, Germany. We have now found that it is advantageous to analyse the cell density by means of a suitable probe introduced into the bioreactor itself (or into a loop through which the medium and suspended cells are passed and then returned to the bioreactor). Such probes are available commercially from Aber Instruments, for example the Biomass Monitor 220, 210 220 or 230. The cells in the culture act as tiny capacitors under the influence of an electric field, since the non-conducting cell membrane allows a build-up of charge. The resulting capacitance can be measured; it is dependent upon the cell type and is directly proportional to the concentration of viable cells. A probe of 10 to 25 mm diameter uses two electrodes to apply a radio frequency field to the biomass and a second pair of electrodes to measure the resulting capacitance of the polarized cells. Electronic processing of the resulting signal produces an output which is an accurate measurement of the concentration of viable cells. The system is insensitive to cells with leaky membranes, the medium, gas bubbles and debris.

Typically, the cell density is from $1.0 \times 10^6$ to $5.0 \times 10^6$ cells/ml, suitably $1.0 \times 10^6$ to $3.5 \times 10^6$ cells/ml, suitably $1.4 \times 10^6$ to $2.8 \times 10^6$ cells/ml, preferably $1.6 \times 10^6$ to $2.6 \times 10^6$ cells/ml, most preferably $1.8 \times 10^6$ to $2.4 \times 10^6$ cells/ml. Increasing the concentration of cells toward the higher end of the preferred ranges can improve volumetric productivity. Nevertheless, ranges of cell density including any of the above point values as lower or higher ends of a range are envisaged.

The culture is typically carried out in a bioreactor, which is usually a stainless steel, glass or plastic vessel of 1 (one) to 10000 (ten thousand) liters capacity, for example 5, 10, 50, 100, 1000, 2500, 5000 or 8000 liters. The vessel is usually rigid but flexible plastic bags can be used, particularly for smaller volumes. These are generally of the 'single use' type.

The heterologous or recombinant protein produced by the method of any of the first three aspects of the invention is preferably a blood protein. By "blood protein" we include any protein that is or may be present in the blood of a human or animal, including proteins that are engineered for intravenous use. Suitable blood proteins include serum albumin, coagulation factors I, II, III, V, VII, VIII, IX, X, XI, XII and XIII, furin, von Willebrand factor, tissue plasminogen activator, interleukins, interferons, metalloproteases such as ADAMTS proteases (e.g. ADAMTS-13), immunoglobulins such as IgG, IgM, IgA or IgE and immunoglobulin fragments. Suitable antibody or immunoglobulin fragments include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). Immunoglobulins and their fragments may be "humanised". In other words, variable domains of rodent origin may be fused to constant domains of human origin such that the resultant antibody retains the antigenic specificity of the rodent parent antibody (Morrison et al (1984) *Proc. Natl. Acad. Sci. USA* 81, 6851-6855).

In a preferred embodiment, the cell culture is used to produce Factor VIII, optionally together with von Willebrand Factor (vWF). The vWF can be added separately to the culture medium and is preferably recombinant. Alternatively, the vWF can be co-produced by including vWF-secreting cells in the culture, as well as the FVIII-secreting cells. Preferably, however, the FVIII and vWF are co-expressed, i.e. each cell secretes both FVIII and vWF. Recombinant vWF can be obtained as in Schlokat, et al. (1995), "Large Scale Production of Recombinant von Willebrand Factor", *Thrombosis* and *Haemostasis* 78, 1160 or U.S. Pat. No. 6,114,146 (Baxter AG). The latter patent also discloses cells that can be used to co-produce vWF with FVIII-secreting cells. Cells that co-express both proteins are disclosed in U.S. Pat. No. 5,250,421 (Genetics Institute) and Kaufman et al (1989) *Mol. Cell. Biol.* 9, 1233-1242.

The term Factor V/II is used herein to denote any polypeptide or complex of polypeptides that has clotting factor VIII activity. Activated Factor VIII functions as a cofactor in the conversion of Factor X to Factor Xa by activated Factor IXa in the presence of phospholipids and calcium ions. Conveniently, the quantity of active Factor VIII can be estimated from the degree to which it promotes conversion of Factor X to Factor Xa in a suitable assay. In a typical assay, Factor Xa hydrolyses a specific chromogenic substrate, thereby liberating a chromophore, the quantity of which is determined spectrophotometrically. Commercially available assay kits include Factor VIII Chromogenic Assay kit (Dade Behring, Switzerland; U.S. Pat. No. 6,100,050); and Coatest Factor VIII kit (Chromogenix, Sweden). Factor VIII concentration in humans is defined as 1 IU/mL blood. The Coatest Factor VIII kit can determine FVIII activity equivalent to at least 0.01 IU/ml blood. To be considered as a Factor VIII as defined above, a polypeptide or complex of polypeptides must have at least 1% of the activity of native Factor VIII such that, when present in blood at the same nanomolar concentration as native Factor VIII, its activity is detectable by the Coatest Factor VIII assay.

A suitable FVIII for production by the method of the invention is native, full length FVIII. Porcine FVIII may be produced in accordance with the invention but the FVIII is more preferably human. As an alternative to native FVIII, variants and analogues can be produced. Many are known in this art, for example the variants and deletion derivatives described in U.S. Pat. Nos. 5,422,260, 4,749,780, 4,868,112, 4,877,614 and 5,171,844. The term "deletion derivative of recombinant Factor VIII" is defined as one or more polypeptide chains having Factor VIII activity, derived from full-length Factor VIII polypeptide by deleting one or more amino acids. Preferably, the said deletion derivative is devoid of most of the B-domain, but retains parts of the amino-terminal and carboxy-terminal sequences of the B-domain that are essential for in vivo proteolytic processing of the primary translation product into two polypeptide chains. The production of such a Factor VIII deletion derivative, identified as "r-VIII SQ", is described in WO 91/09122. The term "r-VIII SQ" is defined as a polypeptide chain derived from full-length Factor VIII and lacking amino acids 743 through 1636. Further FVIII variants lacking all or part of the B domain are described in U.S. Pat. No. 6,358,703.

Suitable vectors for transforming CHO and 293S cells are disclosed in U.S. Pat. No. 5,854,021. BHK cells expressing FVIII may be prepared as disclosed in Wood et al (1984) *Nature* 312, 330-337 or obtained from the ATCC as culture CRL-8544. CHO cells expressing B-domain-deleted variants of FVIII are described in Lind et al (1995) *Eur. J. Biochem.* 232, 19-27 and in U.S. Pat. No. 5,661,008. Three such cell types were deposited with Deutsche Sammlung von Mikroorganismen und Zellkulturen as DSM 6415, DSM 6417, and DSM 6416.

When FVIII and vWF are co-produced, the complex between them may be purified by centrifuging the medium to remove the cells and then exposing the resulting liquid to an immobilised solid support containing an antibody for either FVIII or vWF, or a peptide that will specifically bind FVIII or vWF, under conditions that will not cause the complex to dissociate. Suitable methods are taught in U.S. Pat. No. 6,307,032 (Baxter AG) and U.S. Pat. No. 5,200,510 (ZymoGenetics).

The FVIII (optionally in complex with vWF) may then be formulated and used in known ways. For example, FVIII, having been produced in a culture free of animal proteins, is preferably formulated in a protein-free composition, as disclosed for example in U.S. Pat. No. 6,586,573 (Baxter International), WO 94/07510 or U.S. Pat. No. 6,599,724, and used to treat patients with haemophilia A.

Where the method of the invention is used to produce FVIII, it is preferred that the cell culture supernatant is maintained at a temperature that is set at 36±0.9° C., preferably 36±0.5° C., more preferably 36±0.2° C. and most preferably 36° C. and/or the pH is set at 7.20±0.05, preferably 7.20±0.03, more preferably 7.20±0.01, most preferably 7.20; and/or the cell culture supernatant has a dissolved $CO_2$ concentration of 1 to 10%, preferably 4.0 to 9.0%, more preferably 5.5 to 8.5%. Preferably, at least two of these parameters are within the preferred limits, namely temperature and pH, temperature and $dCO_2$ or pH and $dCO_2$. Most preferably, all three parameters are operated within the preferred limits.

As shown in the Examples, it is advantageous to include copper in the cell culture supernatant when the invention is used to produce FVIII. Typically, cells are cultured in a cell culture supernatant comprising 4 ppb $Cu^{2+}$. Advantageously, the concentration of concentration of $Cu^{2+}$ in the cell culture supernatant is at least 5 ppb, and preferably at least 7, 10, 15 or 25 ppb.

In an alternative preferred embodiment, the cell culture is used to produce ADAMTS-13.

ADAMTS-13, also known as von Willebrand factor cleaving protease (VWF-cp) is a member of the metalloprotease family. It has the ability to metabolize large VWF multimers to smaller forms, by cleaving the peptide bond between residues Tyr-842 and Met-843 of VWF. This metalloprotease is activated by $Ca^2$/$Ba^2$, and is not inhibited by inhibitors of serine or cysteine proteases. Deficient von Willebrand factor (VWF) degradation has been associated with thrombotic thrombocytopenic purpura (TTP). In hereditary TTP, ADAMTS-13 is absent or functionally defective, whereas in the nonfamilial, acquired form of TTP, an autoantibody inhibiting ADAMTS-13 activity is found transiently in most patients.

The cloning and expression of the human ADAMTS-13 gene are described in Plaimauer et al, 2002, Blood. 15; 100 (10):3626-32. The cloning and expression of the human ADAMTS-13 gene, together with the complete sequence of the cDNA are also disclosed in US 2005/0266528 A 1 (Laemmle et al). A suitable ADAMTS-13 for production by the method of the invention is native, full length ADAMTS-13, preferably human ADAMTS-13. As an alternative to native FVIII, variants and analogues can be produced.

The term ADAMTS-13 is used herein to denote any polypeptide or complex of polypeptides that has ADAMTS-13 activity, particularly the ability to cleave the peptide bond between residues Tyr-842 and Met-843 of VWF. Conveniently, the quantity of active ADAMTS-13 may be determined by functional assays, such as functional assays employing modified von Willebrand factor peptides as substrate for ADAMTS-13 (Tripodi et al J Thromb Haemost. 2008 September; 6(9):1534-41). A preferred method of determining r-hu ADAMTS13 activity is disclosed in Gerritsen et al. Assay of von Willebrand factor (vWF)-cleaving protease based on decreased collagen binding affinity of degraded vWF: a tool for the diagnosis of thrombotic thrombocytopenic purpura (TTP). Thromb Haemost 1999; 82:1386-

1389. In this assay, 1 U corresponds to the level of ADAMTS-13 activity in pooled normal human plasma. To be considered as a ADAMTS-13 as defined above, a polypeptide or complex of polypeptides must have at least 1% of the activity of native ADAMTS-13. The quantity of ADAMTS-13 may also be determined by measurement of ADAMTS-13 antigen, for example using the ELISA method disclosed in Rieger et al, 2006, Thromb Haemost. 2006 95(2):212-20.

Proteolytically active recombinant ADAMTS-13 may be prepared by expression in mammalian cell cultures, as described in Plaimauer et al, 2002, supra and US 2005/0266528 A1. Methods of recombinant culture of ADAMTS-13 expressing cells are disclosed in Plaimauer B, Scheiflinger F. Semin Hematol. 2004 January; 41(1):24-33. Preferred cell types for the expression of ADAMTS-13 include HEK-293 cells and CHO cells.

US 2005/0266528 A1 and Zheng et al, 2001, Blood, 98:1662-1666 disclose methods of purifying ADAMTS-13. Purified ADAMTS-13 may be formulated according to conventional methods and used therapeutically, for example to treat TTP.

Where the method of the invention is used to produce ADAMTS-13, it is preferred that the cell culture supernatant is maintained at a temperature that is set at 36.01±0.9° C., preferably 36.01±0.5° C., more preferably 36.01±0.2° C. and most preferably 36.0° C. and/or the pH is set at 7.15±0.05, preferably 7.15±0.03, more preferably 7.15±0.01, most preferably 7.15; and/or the cell culture supernatant has a dissolved $CO_2$ concentration of 1 to 10%, preferably 4.0 to 9.0%, more preferably 5.5 to 8.5%. Preferably, at least two of these parameters are within the preferred limits, namely temperature and pH, temperature and $dCO_2$ or pH and $dCO_2$. Most preferably, all three parameters are operated within the preferred limits.

In an alternative preferred embodiment, the cell culture is used to produce furin.

Furin, also termed PACE (paired basic amino acid cleaving enzyme), belongs to the group of the subtilisin-like serine proteases, which play an important role in the cleavage of proproteins, especially in secretory synthesis (Van de Ven et al., Crit. Rev. Oncogen., 4:115-136, 1993). It is a calcium-dependent serine endoprotease structurally arranged into several domains, namely a signal peptide, propeptide, catalytic domain, homo-B or P-domain, the C-terminally located cysteine-rich domain, transmembrane domain and cytoplasmic tail. The protease cleavage site comprises a recognition sequence which is characterized by the amino acid sequence Arg-X-Lys/Arg-Arg. The protease furin cleaves proproteins specifically after this consensus sequence (Hosaka et al., 1991, J. Biol. Chem. 266:12127-12130).

Intact furin is incorporated into the membrane system of the Golgi apparatus and there it is functionally active (Bresnahan et al, J Cell Biol. 1990; 111:2851-9). Upon transit of the newly synthesized furin precursor from the endoplasmic reticulum to the Golgi compartment, the propeptide is autocatalytically removed in a two step processing event (Anderson et al, EMBO J. 1997; 16: 1508-18). Furin also cycles between the trans-Golgi network and the cell surface via endosomal vesicles, thereby processing both precursor proteins during their transport through the constitutive secretory pathway as well as molecules entering the endocytic pathway. The cellular distribution of furin to the processing compartments is directed by defined structural features within its cytoplasmic tail (Teuchert et al, J Biol Chem. 1999; 274: 8199-07).

Since an overexpression of the native furin protease negatively affects the growth of continuously growing cell cultures, solutions have been sought to reduce the toxic influence of furin on the cells. The C-terminal domains have been found to be dispensable for the functional activity of furin and a truncated form of the over-expressed native furin of 75-80 kD could be detected in the cell supernatant as secreted protein (Wise et al, PNAS. 1990; 87:9378-82). This naturally secreted truncated furin is also known as "shed furin" (Vidricaire et al, Biochem Biophys Res Comm. 1993; 195:1011-8; Plaimauer et al, Biochem J. 2001; 354:689-95) and is cleaved N-terminally of the transmembrane portion (Vey et al, J Cell Biol. 1994; 127: 1829-42).

Furin proteins truncated by genetic engineering, in which the encoding part of the transmembrane and cytoplasmatic domains has been deleted have been described for example for amino acids Δ714-794 (Leduc et al, J Biol Chem. 1992; 267: 14304-8; Molloy et al, J Biol Chem. 1992; 267:16396-402) and for amino acids Δ716-794 ("Sol-PACE", Wasley et al., J Biol Chem. 1993; 268:8458-65; Rehemtulla and Kaufman, Blood. 1992; 79:2349-55) and for amino acids Δ705-794 (Hatsuzawa et al, J Biol Chem. 1992; 267:16094-9). Furin mutants additionally comprising a deletion of the cystein-rich region have also been described (Hatsuzawa et al, J Biochem. 1992; 101:296-301; Creemers et al, J Biol Chem. 1993; 268:21826-34).

WO 2008/141824 (Baxter International Inc., Baxter Healthcare S.A.) discloses a truncated human furin lacking amino acids 578 to 794, i.e. Δ578-794.

The term "furin" is used herein to denote any polypeptide or complex of polypeptides that has furin proteolytic activity.

The evaluation of proteolytic activity of a furin, truncated furin or furin derivative can be performed by any suitable test, for example by using fluorogenic substrates which are comprised of a dibasic cleavage site for which furin is specific (Schlokat et al., Biotechnol Appl Biochem. 1996; 24:257-67). With said assay 1 Unit is defined as the amount of furin that will release 1 pmol of 7-Amino-4-methylcoumarin (AMC) from the fluorogenic substrate Boc-Arg-Val-Arg-Arg-AMC in 1 minute at 30° C. The limit of quantification for this test is typically 0.625 U/mL. Alternatively the proteolytic activity can also be measured by incubating furin with pro-proteins, for example pro-rvWF, for a sufficient time. The degree of pro-rvWF processing can be analyzed for example by Western blotting. The quantity of furin antigen can be measured by an ELISA test. A suitable ELISA test is the human furin DuoSet available from R&D systems, MN (cat. no. DY1503) in which mouse anti-human furin is used as a capture antibody, and biotinylated goat anti-human furin is used as a detection antibody.

A suitable furin for production by the method of the invention is native, full length furin, preferably human furin. As an alternative to native furin, variants and analogues can be produced, including those described above.

Suitable vectors for transforming mammalian cells, particularly CHO cells, with furin or variants of furin are described in WO 2008/141824 (Baxter International Inc., Baxter Healthcare S.A.), together with methods for purifying the furin so produced. WO 91/06314 (Holland Biotechnology) describes furin expression vectors, a method of expressing furin in mammalian cells, particularly COS-1 cells, and the purification of recombinantly produced furin. WO 92/09698 (Genetics Institute and Chiron Corp) describes the expression of furin in CHO cells, either alone, or in combination with vWF or Factor IX.

Pro-rVWF is processed to its mature form during cell culture by endogenously produced furin, which is expressed at relatively low levels in many cell types (Wise et al, 1990, PNAS 87:9378-9382). Pro-rVWF processing can be made more efficient by coexpressing heterologous furin with the Pro-rVWF. Alternatively, WO 2008/141824 suggests that a purified furin may be suitable for use as a reagent to promote processing of rVWF.

Where the method of the invention is used to produce furin, it is preferred that the cell culture supernatant is maintained at a temperature that is set at 35.1±0.9° C., preferably 35.1±0.5° C., more preferably 35.1±0.2° C. and most preferably 35.1° C. and/or the pH is set at 7.15±0.05, preferably 7.15±0.03, more preferably 7.15±0.01, most preferably 7.15; and/or the cell culture supernatant has a dissolved $CO_2$ concentration of 1 to 10%, preferably 4.0 to 9.0%, more preferably 5.5 to 8.5%. Preferably, at least two of these parameters are within the preferred limits, namely temperature and pH, temperature and $dCO_2$ or pH and $dCO_2$. Most preferably, all three parameters are operated within the preferred limits.

In an alternative preferred embodiment, the cell culture is used to produce Factor VII.

"Factor VII polypeptide" encompasses wild-type Factor VII (i.e. a polypeptide having the amino acid sequence disclosed in U.S. Pat. No. 4,784,950), as well as variants of Factor VII exhibiting substantially the same or improved biological activity relative to wild-type Factor VII, and Factor VII variants having substantially modified or reduced biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII polypeptide" also encompasses polypeptides, including variants, in which the Factor VIIa biological activity has been substantially modified or somewhat reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively). Biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of Factor VIIa (or the Factor VII polypeptide) to produce activated Factor X (Factor Xa) in a system comprising TF embedded in a lipid membrane and Factor X (Persson et al., J. Biol. Chem. 272:19919-19924, 1997); (ii) measuring Factor X hydrolysis in an aqueous system; (iii) measuring the physical binding of Factor VIIa (or the Factor VII polypeptide) to TF using an instrument based on surface plasmon resonance (Persson, FEBS Letts. 413: 359-363, 1997); (iv) measuring in vitro hydrolysis of a synthetic substrate by Factor VIIa (or a Factor VII polypeptide); or (v) measuring generation of thrombin in a TF-independent in vitro system. Alternatively, FVII antigen may be determined by ELISA. A suitable ELISA is the AssayMax Human Factor VII (FVII) ELISA Kit available from Assay Pro (St Charles, Mo.) Cat. no EF1007-1, which uses a monoclonal anti-human FVII as capture antibody, and a biotinylated polyclonal anti-human FVII as detection antibody.

A preferred in vitro proteolysis assay for native (wild-type) factor VIIa and/or factor VIIa variant is carried out in a microtiter plate (MaxiSorp, Nunc, Denmark), as described in US 2007/0219135 (Novo Nordisk HealthCare A/G). Factor VIIa (10 nM) and factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate. The absorbance developed during 10 minutes, after subtraction of the absorbance in a blank well containing no FVIIa, may be used to calculate the ratio between the proteolytic activities of variant and wild-type factor VIIa:

$$\text{Ratio} = (A_{405\,nm} \text{ factor VIIa variant})/(A_{405\,nm} \text{ factor VIIa wild-type}).$$

In a variation of this assay, FVII is determined. A thromboplastin is included. FVII in the sample forms a complex with Ca2+ ions and tissue factor which generates small amounts of FXa. The FXa activates FVII to FVIIa.

A commercially available FVII activity assay is the HEMOCLOT FVII reagent kit, available from Aniara (Mason, Ohio) Cat. no. ACK081K in which clotting triggered by a calcium thromboplastin is measured.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X. Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); Factor VIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); Factor VII variants as disclosed in PCT/DK02/00189; and Factor VII variants exhibiting increased proteolytic stability as disclosed in WO 02/38162 (Scripps Research Institute); Factor VII variants having a modified Gla-domain and exhibiting an enhanced membrane binding as disclosed in WO 99/20767 (University of Minnesota); and Factor VII variants as disclosed in WO 01/58935 (Maxygen ApS).

Non-limiting examples of Factor VII variants having increased biological activity compared to wild-type Factor VIIa include Factor VII variants as disclosed in WO 01/83725, WO 02/22776, WO 02/077218, WO 03/27147, WO 03/37932; WO 02/38162 (Scripps Research Institute); and Factor VIIa variants with enhanced activity as disclosed in JP 2001061479 (Chemo-Sero-Therapeutic Res Inst.). Non-limiting examples of Factor VII variants having substantially reduced or modified biological activity relative to wild-type Factor VII include RI 52E-FVIIa (Wild-goose et al., Biochem 29:3413-3420, 1990), S344A-FVIIa (Kazama et al, J. Biol. Chem. 270:66-72, 1995), FFR-FVIIa (Hoist et al, Eur. J. Vase. Endovasc. Surg. 15:515-520, 1998), and Factor VIIa lacking the Gla domain, (Nicolaisen et al, FEBS Letts. 317: 245-249, 1993).

Following production of FVII, the polypeptide may be purified from the medium Purification of Factor VII polypeptides may involve, e.g., affinity chromatography on an anti-Factor VII antibody column (see, e.g., Wakabayashi et al., J. Biol. Chem. 261:11097, 1986; and Thim et al., Biochem. 27:7785, 1988) and activation by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII may be activated by passing it through an ion-exchange chromatography column, such as Mono Q® (Pharmacia) or the like.

Factor VII or activated Factor VII may be formulated and used it known ways. For example, it may be used in treatment of bleeding in hemophiliacs.

Where the method of the invention is used to produce Factor VII, it is preferred that the cell culture supernatant is maintained at a temperature that is set at 36.5±0.9° C., preferably 36.5±0.5° C., more preferably 36.5±0.2° C. and most preferably 36.5° C. and/or the pH is set at 7.20±0.05, preferably 7.20±0.03, more preferably 7.29±0.01, most preferably 7.29; and/or the cell culture supernatant has a dissolved $CO_2$ concentration of 1 to 10%, preferably 4.0 to 9.0%, more preferably 5.5 to 8.5%. Preferably, at least two of these parameters are within the preferred limits, namely temperature and pH, temperature and $dCO_2$ or pH and $dCO_2$. Most preferably, all three parameters are operated within the preferred limits.

The present invention will be further illustrated in the following examples, without any limitation thereto.

Example 1

Basic Cell Culture

FVIII Production

Typical cultures are established in bioreactors, using a subclone of the 10A1C6 CHO cell line transformed to co-express Factor VIII and von Willebrand Factor described in Kaufman et al (1989) *Mol. Cell. Biol.* 9:1233-1242 and U.S. Pat. No. 5,250,421. The particular subclone was obtained by adaptation to a standard medium that does not contain animal-derived products, and subcloning in a microplate.

The standard culture medium is:

| DMEM/Ham's F12 50/50 | 11.76 g/kg |
|---|---|
| to which was added: | |
| L-glutamine | 0.6 g/kg |
| Ethanolamine | 1.53 mg/kg |
| Synperonic F68 | 0.25 g/kg |
| $NaHCO_3$ | 2 g/kg |
| Soya peptone | 4 g/kg |
| $CuSO_4 \cdot 5H_2O$ | 17.02 mg/kg |

The basal DMEM/Ham's F12 50/50 medium contains 1.3 mg/kg $Cu^{2+}$ sufficient for the complete medium to contain 4.3 ppb $Cu^{2+}$.

ADAMTS-13 Production

CHO DUKX-B11 cells were transfected using the calcium phosphate coprecipitation method, to introduce the ADAMTS-13 gene. Cells were cultured under neomycin selection conditions and were selected after methotrexate and G418 treatment. After serum-free adaptation, cells were subcloned and subclone 640-2 was chosen as production clone.

The standard culture medium is a serum-, insulin- and oligopeptide-free medium based on the medium disclosed in US 2007/0212770 (Grillberger et al; Baxter International Inc., Baxter Healthcare S.A.)

Furin Production

CHO DUKX-B11 cells were transfected using the calcium phosphate coprecipitation method, to introduce the furin gene. Cells were selected with DHFR medium without hypoxanthine, thymidine and glycine. Production clone 488-3 was identified by subcloning and selection in medium containing 100 nM methotrexate, followed by serum-free adaptation.

The standard culture medium is a serum-, insulin- and oligopeptide-free medium based on the medium disclosed in US 2007/0212770 (Grillberger et al; Baxter International Inc., Baxter Healthcare S.A.)

FVII Production

CHO DUKX-B11 cells were transfected with a bicistronic vector to allow coexpression of FVII and VKORC (vitamin K epoxide reductase complex). Gene expression is driven by the CMV promoter, and an internal ribosomal entry site (IRES) is located between the FVII gene and the VKORC gene Cells were transfected using the calcium phosphate precipitation method. The selection medium contained 200 µg/ml hygromycin B. Cells were subcloned under serum-free conditions and a high expressing subclone 1E9 was chosen as production clone. 1E9 was selected as having advantageous properties with regard to growth, productivity and stability under continuous culture conditions. Stability was evaluated for a period of two months in chemostat mode.

The standard culture medium is based on the culture medium disclosed in U.S. Pat. No. 6,936,441 (Baxter AG), and contains, inter alia, 2.5 g/L soy peptone and 5 mg/L insulin (Nucellin®; Eli Lilly or Novolin®, Novo Nordisk).

Standard Processes Used for FVIII Production

5 L Continuous Culture

Medium is pre-conditioned for several hours in a $CO_2$ incubator (5-15% $CO_2$) at 37° C. To establish the culture, at least one 1 ml vial ($10^7$ CHO cells/ml) is defrosted and the cells diluted in 60 ml pre-conditioned medium in Roux flasks (200 ml), and cultured in the $CO_2$ incubator at 37° C. After about 3 days, the 60 ml culture is added to 140 ml of fresh medium in 1 roller bottle (1.8 L). The roller bottle is sparged with 15% $CO_2$ and cultured at 37° C. with rotation. After two days, the cells are split ⅓ and cultured in 2 roller bottles in fresh medium (200 ml medium ±100 ml culture=300 ml per roller bottle). After two or three further days, the cells are again split ⅓ and cultured in a total of 6 roller bottles in fresh medium as described above. Once the required cell density of approximately 1×10⁶ cells/ml is reached, the 1800 ml inoculum is inoculated in 3.2 L medium that had been preconditioned as described above, and cultured in the 5 L bioreactor. Under standard conditions, the 5 L bioreactor is run at pH 7.2, a cell density of 1.4×10⁶ cells/ml and a temperature of 37° C. Under standard conditions, the culture is sparged with $O_2$ having a 10 µm bubble size at a rate of 0.25 VVH (volume of $O_2$ per volume of culture per hour).

Inoculum Build-Up in the 40 L Bioreactor

An inoculum pool is obtained essentially as described above in relation to the 5 L continuous culture. However, the pool is approximately 5 L, and is obtained from 18 rather than 6 roller bottles. The BR-40 bioreactor is cleaned and sterilized before the operation, and approximately 8 L of medium is transferred to BR-40 prior to inoculation. The inoculum pool of approximately 5 L is transferred from the pooling tank to the bioreactor via a transfer line to reach a total culture volume of approximately 13 L. Once the cell density reaches ≥9×10⁵ cells/mL, the culture is diluted (1:3) with media. After 1 to 3 more days, the cell concentration again reaches ≥9×10⁵ cells/mL, and the transfer of the inoculum to the 320 L bioreactor is carried out.

Expansion in the 320 L Bioreactor

The BR-320 bioreactor is cleaned and sterilized before the operation, and approximately 80 L of medium is transferred to BR-320 prior to inoculation. The inoculum of approximately 40 L is transferred from the BR-40 bioreactor to the BR-320 bioreactor via a transfer line to reach an initial culture volume of approximately 120 L. Once the cell density reaches ≥9×10⁵ cells/mL, the culture is diluted (1:3) with medium. After 3 to 6 days (total time), the cell concentration again reaches ≥9×10⁵ cells/mL, and the transfer of the inoculum to the 2500 L bioreactor is carried out.

2500 L Bioreactor Build-Up

The inoculum of approximately 320 L is transferred from the BR-320 to the BR1 bioreactor via a transfer line that already contained approximately 630 L of medium to reach an initial culture volume of approximately 950 L. Once the cell density reaches ≥9×10⁵ cells/mL, the culture is diluted (~1:3) with medium to a final volume of approximately 2500 L. After 4 to 7 days (total time), the cell concentration again reaches ≥9×10⁵ cells/mL, and approximately 1150 L of the inoculum is transferred from the BR1 to the BR2 bioreactor that contains approximately 1350 L of medium. After transfer, approximately 1150 L of medium is added to bioreactor BR1, to reach a final culture volume of approximately 2500 L.

Chemostat

The 'chemostat' culture mode is started as soon as the cell concentration in each bioreactor reaches ≥1.2×10⁶ cells/mL. Approximately 1250 L of medium per day is added in a continuous mode to each bioreactor. The cell concentration is between 9×10⁵–1.6×10⁶ cells/mL in each 2500 L bioreactor. Multiple harvests of approximately 1250 L/day/bioreactor are stored in sterile bags at 2-8° C. The culture is maintained for about 50-57 days in the chemostat mode. Under standard conditions, the pH is set to 7.2, the temperature is set to 37° C. and the culture is sparged with $O_2$ having a 10 µm bubble size at a rate of 0.02 VVH (volume of $O_2$ per volume of culture per hour).

Similar cultivation methods are also applicable to the culture of CHO cells expressing ADAMTS-13, furin or FVII.

Example 2

Effects of Changing Various Parameters on FVIII Productivity

FVIII productivity of the FVIII- and vWF-expressing CHO cell clone described in Example 1 was determined under various culture conditions.

In separate experiments, the pH, cell density and temperature were varied in a 5 L scale continuous culture. In each case, the control experiment used pH 7.1, a cell density of 1.4×10⁶ cells/ml and 37° C.

When the cell density was increased, the volumetric FVIII productivity (IU per liter per day), relative to the value for a cell density of 1.2×10⁶ cells/ml, increased as follows:

| Cell density (×10⁶ cells/ml) | Percentage increase in cell density | Productivity increase (%) |
|---|---|---|
| 1.2 | — | — |
| 1.4 | 17 | 43 |
| 1.6 | 33 | 51 |
| 1.8 | 50 | 65 |
| 2.0 | 67 | 73 |
| 2.2 | 83 | 74 |
| 2.4 | 100 | 76 |
| 2.6 | 117 | 49 |

Hence, a substantial increase in productivity could be achieved by increasing cell density. This could not have been predicted, since increasing cell density can reduce the productivity per cell. Moreover, at certain cell densities, the increase in productivity was found to be greater than the increase in cell density, which is even more surprising.

pH was increased to 7.2 by altering the sparge parameters. In the control vessel at pH 7.1, the culture was sparged with $O_2$ having a 10 µm bubble size at a rate of 0.25 VVH (volume of $O_2$ per volume of culture per hour). In the test vessel at pH 7.2 the culture was sparged with air having a 10 µm bubble size at a rate of 1.25 VVH (volume of air per volume of culture per hour). By increasing the pH from 7.1 to 7.2, the productivity could be increased by about 16%.

By lowering the temperature from 37° C. to 36° C., the productivity increased by about 22%.

Example 3

Influence of Cell Density and Copper Concentration on FVIII Productivity

FVIII productivity of the FVIII- and vWF-expressing CHO cell clone described in Example 1 was determined under various culture conditions.

A control culture was operated at pH 7.1, 37° C., 4 ppb $Cu^{2+}$ and a cell density of 1.4×10⁶ cells/ml.

Comparative cultures were run at pH 7.2 and 36° C. In one culture the cell density was increased to 1.6×10⁶ cells/ml and in another it was increased to 2.0×10⁶ cells/ml. In a third culture, the cell density was 2.0×10⁶ cells/ml and the copper concentration was increased from 4 ppb to 6 ppb.

Results: by reducing the temperature, increasing the pH and increasing the cell density to 1.6×10⁶ cells/ml (an increase of 14%), the FVIII productivity increased by 41-50%. A further increase in cell density to 2.0×10⁶ cells/ml (43%) gave an increase in productivity (compared to the control culture) of 39-77%. When the copper in a 2.0×10⁶ cells/ml culture was increased to 6 ppb, the productivity (compared to the control culture) was increased by 48-98%.

Hence, by raising the pH slightly, decreasing the temperature slightly, increasing the cell density by only 43% and increasing the copper concentration by 50% the FVIII productivity can be almost doubled.

Example 4

Influence of Cell Density and Copper Concentration on vWF Productivity

Example 3 was repeated but the volumetric vWF productivity was measured. At $1.6 \times 10^6$ cells/ml and 4 ppb copper (36° C., pH7.2) the productivity was 124% of the control. At $2.0 \times 10^6$ cells/ml and 6 ppb copper the productivity was 182%.

Hence, again substantial increases in productivity can be achieved by making seemingly small changes in the process parameters.

Example 5

Influence of Cell Density, pH and $dCO_2$

FVIII productivity of the FVIII- and vWF-expressing CHO cell clone described in Example 1 was determined under various culture conditions.

In this experiment, the cell density was increased from $1.41 \times 10^6$ cells/ml to $2.03 \times 10^6$ cells/ml, the pH was increased from 7.1 to 7.2 and the $dCO_2$ concentration was reduced from 9.5% to 6.2%.

The volumetric FVIII productivity (IU per liter per day) increased by 98% and the specific FVIII productivity (IU per million cells per day) increased by 36%.

Example 6

Influence of pH and Temperature on Furin Production

Furin expressing CHO cells were cultivated in 2.5 L bioreactors in chemostatic mode. The cell density was maintained at an average of between $1.52 \times 10^6$ and $1.78 \times 10^6$ cells/ml for individual cultures over 5 cultivation days. Dissolved oxygen was controlled in all experiments at a set-point of 20% air saturation. Dissolved $CO_2$ concentration was maintained between 5%-6% by overlaying the headspace of the bioreactors with $CO_2$.

By means of the "design of experiments method", different temperatures were combined with different pH values to ascertain the conditions which result in maximum volumetric productivity of furin. Five temperatures were combined with three pH values according to the "Doehlert Matrix", resulting in seven combinations of temperature and pH as follows:

| Fermentation lot | Temp (° C.) | pH |
| --- | --- | --- |
| 1 | 35.1 | 7.20 |
| 2 | 35.8 | 7.10 |
| 3 | 35.8 | 7.30 |
| 4 | 36.5 | 7.20 |
| 5 | 36.5 | 7.20 |
| 6 | 37.2 | 7.10 |
| 7 | 37.2 | 7.30 |
| 8 | 37.9 | 7.20 |

The combination of 36.5° C. and pH 7.20 was chosen as the center point, which was applied to two fermentation lots (4 and 5 in the above table).

The data, including volumetric and specific productivity, and growth rate, were analyzed statistically with the Response Surface Methodology (RSM), using the "Minitab" software.

Temperature, but not pH, significantly influenced growth rate, with a maximum for the growth rate occurring at 36.5° C. By decreasing the temperature from 37° C. to 35.1° C., the volumetric productivity could be raised by approximately 2.7-fold. A similar trend was seen for specific productivity. This is a surprising result, as it might have been expected that the maximum volumetric productivity would be observed at the temperature at which growth rate was maximal. The influence of the pH for specific and volumetric productivity was minor in the investigated range of 7.20+/−0.1. A slightly higher productivity was observed in the lower pH range of 7.15+/−0.05 (or between 7.10 and 7.20), therefore pH 7.15 was selected as set-point for furin production.

Example 7

Influence of $dCO_2$ on Furin Production

Two fermentation runs were carried out in parallel in chemostat mode in 2.5 L bioreactors, one run with a $CO_2$ concentration of approximately 7.5% and the other with a $CO_2$ concentration of approximately 12%. The $CO_2$ concentration was adjusted by varying the $CO_2$ fraction in the head space flow. The fermentations were carried out at 37° C., at a pH of 7.15 and with a $pO_2$ of 20%. The cell count was approximately $1.07 \times 10^6$ cells/ml over 12 days in the high $CO_2$ culture, and $1.49 \times 10^6$ cells/ml in the low $CO_2$ culture.

Reducing the $CO_2$ concentration from 12% to 7.5% had the effect of increasing the volumetric productivity by approximately 2.78-fold and the specific productivity by 2-fold. Cell growth rate was also higher in the low $CO_2$ culture.

Example 8

Influence of pH and Temperature on FVII Production

FVII expressing CHO cells were cultivated in 2.5 L bioreactors in chemostat mode, where the cell density was maintained at an average of about $2.5 \times 10^6$ cells/ml (between $2 \times 10^6$ and $3 \times 10^6$ cells/ml) for individual cultures over 4 cultivation weeks. Dissolved oxygen was controlled in all experiments at a setpoint of 20% air saturation. Dissolved $CO_2$ concentration was maintained between 4%-7% by overlaying the headspace of the bioreactors with $CO_2$.

By means of the "design of experiments method", different temperatures were combined with different pH values to ascertain the conditions which result in maximum volumetric productivity of FVII. Three temperatures were combined with three pH values according to the "Doehlert Matrix", resulting in five combinations of temperature and pH as follows:

| Fermentation lot | Temp (° C.) | pH |
| --- | --- | --- |
| 1 | 36.0 | 7.15 |
| 2 | 36.0 | 7.25 |
| 3 | 36.5 | 7.20 |
| 4 | 37.0 | 7.15 |
| 5 | 37.0 | 7.25 |

The mean maximum volumetric kinetic productivity was achieved at 36.5° C. and a pH setpoint of 7.20. There was a positive interaction of the parameters, such that the result of optimising both parameters was greater than the combined effects of optimising each parameter individually.

Example 9

Influence of $dCO_2$ on FVII Production

The effect of four different $CO_2$ concentrations (5.0, 6.3, 7.6 and 8.9%) on FVII productivity was tested in small scale continuous culture.

Cells were cultivated until chemostat day eight, and then transferred into 2.5 L Rushton Bioreactors and cultivated under continuous conditions at pH 7.20 and 36.5° C. for almost four weeks. Data from only the last three weeks were analysed due to the necessary equilibration to the different $CO_2$ concentrations during the first week. $CO_2$ levels were controlled by off line measurement and addition of $CO_2$ into the headspace of the bioreactors.

The recorded cell densities varied from $2.36 \times 10^6$ cells/ml at a $CO_2$ level of 8.9% to $2.87 \times 10^6$ cells/ml at 5.0%. The growth rates for the same range are 0.42 $d^{-1}$ and 0.49 $d^{-1}$. Increased specific growth rates at low $CO_2$ level correlated with increased specific productivities. The compound effects of $CO_2$ on growth rate and specific productivity resulted in a substantial effect on volumetric productivity.

A decrease in the $CO_2$ concentration from 8.9% to 5% increases the specific growth rate by 17%, the specific productivity by 10% and the volumetric kinetic productivity by 35%.

Example 10

Influence of Temperature and pH on ADAMTS-13 Production

Transfected CHO cells expressing recombinant ADAMTS-13 were cultivated in chemostat cultures in 1.5 L bioreactors.

In a first experiment, pH and temperature were set to different setpoints in the range of 36° C. to 38° C. and pH 7.10 to 7.30. Samples from the steady state were analyzed for cell count and ADAMTS-13 expression by ELISA, and dilution rates from the chemostat cultures were measured to calculate the growth rate and volumetric ADAMTS-13 expression. Once the optimum was found to be at the outer range of the design space, a second experiment was set up with a temperature range from 35° to 37° C. and pH 7.05 to 7.15, and data were analyzed from the steady state. Cell densities ranged from $1.17-1.71 \times 10^6$ cells/ml. $CO_2$ was controlled by overlaying the headspace with $CO_2$ to reach a dissolved $CO_2$ concentration of 4-6%.

Data from both experiments were normalized and analyzed using statistical software Minitab.

Specific growth rate was found to have its optimum at pH 7.13 and 36.0° C. using a quadratic model for pH and temperature. The effect of temperature on growth rate was weak.

Volumetric productivity was found to have its optimum at pH 7.15 and 36.0° C. Despite the weak effect of temperature on growth rate, there was a relatively strong effect of temperature on volumetric productivity.

Assuming a constant temperature of 37° C., the effect of raising pH from 7.10 to 7.15 was to increase volumetric productivity by 10%. Assuming a constant pH of 7.10, the effect of decreasing temperature from 37° C. to 36° C. was to increase volumetric productivity by 14%. The overall effect of changing conditions from pH 7.10 and temperature of 37° C. to pH 7.15 and temperature of 36° C. was to increase volumetric productivity by 24%.

The contents of all references cited herein are included by reference.

The invention claimed is:

1. A method comprising:
expressing heterologous Factor VIII protein in a mammalian cell in continuous cell culture wherein the continuous cell culture is maintained at a temperature of 36.0±0.5° C. and a cell culture density of from $1.4 \times 10^6$ to $2.6 \times 10^6$ cells/ml, and wherein the mammalian cell is a CHO cell.

2. The method of claim 1, wherein the temperature of the continuous cell culture is maintained at 36±0.2° C.

3. The method of claim 1, wherein the temperature of the continuous cell culture is maintained at 36° C.

4. The method of claim 1, wherein the temperature of the continuous cell culture is maintained at 36.5° C.

5. The method of claim 1, wherein the continuous cell culture is maintained at a pH of from 7.10 to 7.25.

6. The method of claim 5, wherein the pH of the continuous cell culture is maintained at 7.20±0.05.

7. The method of claim 5, wherein the pH of the continuous cell culture is maintained at 7.20±0.03.

8. The method of claim 5, wherein the pH of the continuous cell culture is maintained at 7.20±0.01.

9. The method of claim 5, wherein the pH of the continuous cell culture is maintained at 7.20.

10. The method of claim 5, wherein the pH of the continuous cell culture is maintained at 7.15±0.05.

11. The method of claim 5, wherein the pH of the continuous cell culture is maintained at 7.15±0.03.

12. The method of claim 5, wherein the pH of the continuous cell culture is maintained at 7.15±0.01.

13. The method of claim 5, wherein the pH of the continuous cell culture is maintained at 7.15.

14. The method of claim 1, wherein the continuous cell culture is maintained at a dissolved $CO_2$ concentration of from 1% to 10%.

15. The method of claim 14, wherein the $CO_2$ concentration of the continuous cell culture is maintained at from 4.0% to 9.0%.

16. The method of claim 14, wherein the $CO_2$ concentration of the continuous cell culture is maintained at from 5.5% to 8.5%.

17. The method of claim 14, wherein the continuous cell culture is maintained at a pH of from 7.10 to 7.25.

18. The method of claim 17, wherein the cell culture supernatant of the continuous cell culture is buffered with bicarbonate.

19. The method of claim 14, wherein the dissolved $CO_2$ concentration of the continuous cell culture is maintained by sparging the continuous mammalian cell culture with air.

20. The method of claim 1, wherein the cell density of the continuous cell culture is maintained at from $1.6 \times 10^6$ to $2.6 \times 10^6$ cells/ml.

21. The method of claim 20, wherein the cell density of the continuous cell culture is maintained at from $1.8 \times 10^6$ to $2.4 \times 10^6$ cells/ml.

22. The method of claim 1, wherein the Factor VIII is coexpressed with von Willebrand Factor.

23. The method of any one of claims 1, 5, or 14, wherein the cell culture supernatant of the continuous cell culture comprises copper ($Cu^{2+}$) at a concentration of at least 5 ppb.

24. The method of claim 23, wherein the $Cu^{2+}$ concentration of the cell culture supernatant is at least 7 ppb.

25. The method of claim 1, wherein the heterologous protein is FVIII, and the cell culture density of the continuous cell culture is maintained by:
- measuring the cell culture density of the continuous cell culture using an in-line sensor, and
- automatically controlling the influx of fresh medium into the continuous cell culture to maintain the cell culture density of from $1.4\times10^6$ to $2.6\times10^6$ cells/ml.

26. The method of claim 1, wherein the continuous cell culture is operated as a chemostat or a turbidostat continuous cell culture.

* * * * *